US008561610B2

(12) United States Patent
Wachtel et al.

(10) Patent No.: US 8,561,610 B2
(45) Date of Patent: Oct. 22, 2013

(54) MEDICAMENT DISPENSING DEVICE, MEDICAMENT MAGAZINE THEREFOR AND METHOD OF REMOVING A MEDICAMENT FROM A MEDICAMENT CHAMBER

(75) Inventors: Herbert Wachtel, Ingelheim (DE);
Johannes Geser, Ingelheim (DE);
Burkhard Metzger, Ingelheim (DE);
Michael Spallek, Ingelheim (DE);
Michael Krueger, Ingelheim (DE);
Hubert Kunze, Dortmund (DE); Achim Moser, Chemnitz (DE); Elmar Mock, Colombier (CH); Antonino Lanci, Bern (CH); Andre Klopfenstein, La Neuveville (CH)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/482,359

(22) Filed: May 29, 2012

(65) Prior Publication Data

US 2012/0247465 A1 Oct. 4, 2012

Related U.S. Application Data

(63) Continuation of application No. 12/296,983, filed as application No. PCT/CH2007/000182 on Apr. 13, 2007, now abandoned.

(30) Foreign Application Priority Data

Apr. 13, 2006 (EP) .................................... 06405160

(51) Int. Cl.
*A61M 15/00* (2006.01)
*A61M 16/00* (2006.01)

(52) U.S. Cl.
USPC ................................. 128/203.15; 128/203.21

(58) Field of Classification Search
USPC ........................... 128/203.21–203.22, 203.12
See application file for complete search history.

(56) References Cited

U.S. PATENT DOCUMENTS

| 5,301,666 | A | | 4/1994 | Lerk et al. | |
|---|---|---|---|---|---|
| 5,476,093 | A | * | 12/1995 | Lankinen | 128/203.15 |
| 5,575,281 | A | | 11/1996 | Mecikalski | |
| 5,715,810 | A | * | 2/1998 | Armstrong et al. | 128/203.15 |
| 6,655,381 | B2 | * | 12/2003 | Keane et al. | 128/203.15 |
| 7,318,436 | B2 | * | 1/2008 | Snow | 128/203.21 |
| 7,464,706 | B2 | * | 12/2008 | Steiner et al. | 128/203.15 |

FOREIGN PATENT DOCUMENTS

| EP | 0 547 429 A1 | 6/1993 |
|---|---|---|
| EP | 1 475 115 A2 | 11/2000 |

(Continued)

*Primary Examiner* — Stephen Crow
(74) *Attorney, Agent, or Firm* — Michael P. Morris; David L. Kershner

(57) ABSTRACT

A medicament dispensing device, a medicament magazine thereof, and a method of removing a medicament from the medicament magazine. The inhaler has a mouthpiece (9) and an air channel (4) connected thereto, as well as a medicament magazine with at least one medicament chamber containing a powdered medicament. A drive current is produced in the air channel, while a vacuum flow (5') can be produced by the drive current and a constriction formed in the air channel. This narrowest part of the air channel that produces the vacuum flow is connected to a removal opening (2) which communicates with a control opening (3), in order to form an emptying current through the control opening via the removal opening. In a preferred embodiment the at least one medicament chamber including the control opening, the removal opening and a fill opening are housing in the one-piece medicament magazine.

21 Claims, 5 Drawing Sheets

(56) References Cited

FOREIGN PATENT DOCUMENTS

| | | |
|---|---|---|
| GB | 2 340 758 A | 3/2000 |
| WO | 92/10229 A1 | 6/1992 |
| WO | 94/06497 A1 | 3/1994 |
| WO | 01/07107 A2 | 2/2001 |
| WO | 02/098495 A1 | 12/2002 |
| WO | 03/045483 A2 | 6/2003 |
| WO | 2005/002654 A2 | 1/2005 |
| WO | 2006/061637 A2 | 6/2006 |
| WO | 2007/018568 A1 | 2/2007 |

\* cited by examiner

MEDICAMENT DISPENSING DEVICE, MEDICAMENT MAGAZINE THEREFOR AND METHOD OF REMOVING A MEDICAMENT FROM A MEDICAMENT CHAMBER

CROSS REFERENCE TO RELATED APPLICATION

This application is a continuation application of application Ser. No. 12/296,983 filed Dec. 30, 2008, which is the national phase entry under 35 U.S.C. §371 of International Application No. PCT/CH2007/000182, filed Apr. 13, 2007, which claims priority to European Application No. EP 06405160.0, filed Apr. 13, 2006, each of which is hereby incorporated by reference in its entirety.

BACKGROUND OF THE INVENTION

1. Field of the Invention

The invention relates to the field of medicament dispensing devices with a multi-dose magazine, particularly multi-dose powder inhalers, and relates to a medicament dispensing device according to the preamble of the independent claim. Also claimed is a medicament magazine for use in the medicament dispensing device, and a method of removing a medicament, particularly a powdered medicament.

Inhalers are known from the prior art in which a connection is made directly to a medicament chamber by means of a vacuum flow produced by inhaling (Venturi) and a powdered medicament contained therein is removed. In U.S. Pat. No. 6,655,381 a powdered medicament is placed in wells arranged in a circle in an annular magazine. A seal that closes off the wells is removed substantially in its entirety and a Venturi tube is arranged parallel to the magazine with the constriction above the well. Attached to the Venturi tube is a longer turbulence chamber which is needed as the medicament is essentially removed from the well all in one go. With this device it is not possible to achieve accurate dosing of a medicament or adjustment to different dosages.

2. Description of Related Art

In addition, there are various inhalers in which a medicament chamber is opened by piercing. However, openings in a film made by piercing are not very precisely defined, which means that on the one hand the precise amount of a medicament removed is not known and also differences occur between successive removals. This is undesirable particularly with medicaments the activity of which depends to a very high degree on the dosage.

In order to achieve the best possible turbulence in a medicament and thereby dissolve the carrier material and the active substance itself, in EP 1 475 115 and GB 2 340 758, a medicament chamber is essentially divided into an entry and exit chamber which are joined together by a constricted passage. A medicament is placed only in the entry chamber. By piercing or introducing cannulas, an air flow is produced through the medicament chamber from the entry chamber through the constriction into the exit chamber and out of the medicament chamber. In EP 1 475 115, for improved emptying of the medicament chamber, the entry and exit chamber are each provided with two openings. In both specifications, the openings in the chambers are defined by the piercing.

In U.S. Pat. No. 5,715,810 a medicament chamber incorporated in an annular magazine is pierced on both sides. One piercing cannula is attached to a Venturi current, so as to produce an air flow through the chamber. The removal takes place in one step and cannot be metered, or can only be metered poorly. Here, too, the chambers are defined by piercing and pins used for this.

In WO 03/045483 a medicament chamber is pierced and a medicament contained therein is emptied out using an air flow produced by a compressed air source.

EP 0 547 429 discloses a cylindrical medicament magazine in which a fresh medicament chamber is brought into registry with a removal opening inside the apparatus by a screwing movement. In the apparatus, the air flow is subdivided: while one part empties the medicament chamber, the other part is passed through the apparatus and is combined with the medicament air current as an encircling air current.

In WO 2005/002654 an air flow is injected through a medicament chamber. Individual medicament pouches are housed in an annular magazine. During use the pouches are pushed out of the magazine from behind, thereby severing a sealing film and are coupled with a removal mechanism. At the same time an air current is guided into and through the pouch at the maximum possible speed. To trigger aggregation of a powder and prevent medicament from being carried forward into successive inhalations, an individual channel is provided downstream of each pouch. With an additional bypass channel that circumvents the pouch and also opens into a mouthpiece, the total volume of air inhaled is increased and inhalation facilitates or guarantees a sufficient air current being present to transport the medicament to the user. Owing to the fact that some of the air current is deflected through the bypass channel, the air current through the pouch is reduced, so that the removal process is prolonged. The removal of the medicament can thus be spread over a somewhat longer period of time instead of all being removed at once.

The powder inhaler from WO 2005/002654 is relatively complicated in construction. A number of different parts are present, some of which move and have to be coordinated with one another. Moreover, the removal of the medicament is not triggered by an actual Venturi principle, but rather there is an intake current passing directly through the medicament pouches, and this can be weakened by a bypass flow.

The aim of the invention is therefore to provide a medicament dispensing device, a medicament magazine for use in such a medicament dispensing device and a method of removing a medicament form a medicament chamber in which the removal is based on the Venturi principle and the amount taken out can be metered accurately and reproducibly.

This aim is achieved by the medicament dispensing device, the medicament magazine, and the method, as defined in the claims.

The invention is based on the principle known from U.S. Pat. No. 6,655,381, for example, of applying a Venturi-like vacuum flow to a medicament chamber and sucking the medicament contained therein out of the chamber by the vacuum and transporting it with the flow towards a mouthpiece. There, the medicament travels with the air current in the lungs of the user inhaling it.

In the device and method according to the invention, a drive current is now produced in an air channel, which as a result of a constriction in the air channel produces a vacuum flow in this region. The narrowest part of the air channel causing the reduced pressure flow is connected to a removal opening of a medicament chamber. The removal opening is connected to a control opening, so that an emptying current is formed through the control opening via the removal opening and through the medicament chamber. The emptying current is not connected to the drive current before entering the medicament chamber, but combines with the drive current after leaving the removal opening, so that a medicament carried along with the emptying current is transported with the drive current towards the mouthpiece.

The removal and control openings are preferably integrated directly in a medicament magazine. If the openings or the medicament magazine as a whole are produced by injection moulding from plastics, for example, these openings are very precisely defined, in a way which is not possible when an opening is produced by piercing, for example. By integrating the removal and control openings in the medicament magazine, these two openings are pre-defined and are fixed both before and after opening a medicament chamber.

The control and removal openings form a major part of a throttle arrangement by which it is possible to control the emptying current and hence to vary the quantity of medicament removed per unit of time. Other elements of the throttle arrangement with different effects may be the inner configuration of the medicament chamber itself, and the construction of the air channel connected to the removal opening, particularly its diameter.

As a result, the removal can be deliberately controlled, is precisely defined and above all reproducible. A throttle effect and hence an emptying current can be deliberately selected on the basis of the accurately defined but variable elements such as the control opening, removal opening, inner configuration of the medicament chamber and can also easily be changed to other dosages, quantities and types of medicaments.

The inhaler may also have at least one bypass opening to assist the inhalation process, e.g. for children or people with weakened lungs. This bypass opening serves to form a bypass flow which also leads to the mouthpiece and is preferably arranged downstream of a removal opening in the direction of the mouthpiece. However, it does not have any direct influence on a defined correlation between the vacuum flow, the removal opening and control opening.

A medicament chamber is preferably constructed so that at least some of the emptying current flows away over the medicament contained in the medicament chamber. By a suitable inner configuration of the medicament chamber it is also possible to influence the disaggregation and dispersion of a medicament. For example, additional turbulence can be introduced into an emptying current by means of a turbulence element, which is preferably formed by at least one part of the wall of the medicament chamber itself. This can increase the throttling effect or, if necessary, reduce it.

In the medicament chamber an additional vacuum flow can be produced, for example by means of a special configuration of a chamber wall or by means of a turbulence element. This is preferably arranged in a direct line between the control and removal openings, such that a medicament located on the floor of the medicament chamber is detached by this additional vacuum flow in the chamber. This can be achieved by, for example, the medicament chamber itself forming a kind of Venturi tube in all or part of the region between the control and removal openings.

A medicament magazine typically has a fill opening in addition to a control and removal opening. This fill opening is preferably formed independently of the other two openings in the magazine. This has the advantage that the fill opening can be very large, to assist with the filling operation. The fill opening is closed off, preferably sealed with a foil, after the introduction of a powder. If the medicament magazine is constructed as an annular magazine with a plurality of medicament chambers arranged in a circle therein, the control and removal openings of each chamber are spaced from one another, preferably on one side of the magazine, while the fill opening is arranged on the opposite side of the magazine. Thus, the opening of the control and removal openings is also independent of the removal of a sealing foil. Preferably a medicament magazine has a plurality of medicament chambers and single doses contained therein. The number is preferably in the range from 1 to 100 or up to 200 single doses, preferably in the range from 1-60, for example between 7-180 or 14-150, e.g. 30-120, 45-100, 30, 90, 60, 120. For inhalers the maximum number of single doses is preferably 60, for reasons of convenience and therapy.

An inhaler with a medicament magazine of this kind is very versatile in use. Besides the various possibilities of coordination and deliberate and very precise dosing possibilities, particularly their reproducibility, there is also the option of using the inhaler with a wide range of amounts and types of medicament. It is relatively simple to use a different medicament magazine, e.g. with a medicament chamber with a different, e.g. greater or smaller, capacity. If a removal opening is accurately defined by the medicament magazine itself, an adjacent (vacuum) opening in the Venturi suction tube may also be made larger without affecting the removal opening and hence the emptying current. As a result an inhaler can also be used with different medicament magazines, e.g. those with differently designed removal openings. Owing to the fact that only one removal opening has to be coupled at the inhaler end, the remainder of the construction of the inhaler and also the medicament chamber, in relation to a removal mechanism, is substantially independent of the medicament magazine and vice versa. In particular, a medicament chamber may be very elongated, may have an angle, etc., and a control opening may be arranged accordingly at different locations in the magazine. This is possible as the control opening is not directly connected to the arrangement of the Venturi tube, and in particular, the drive current produced in the Venturi tube and the emptying current formed by the coupling of the vacuum flow to the magazine have a different origin.

In the inhaler according to the invention essentially any kind of opening mechanism is possible: a medicament chamber can be opened before the removal of the medicament by piercing, scraping or peeling off a sealing foil that closes off the medicament chamber. A medicament chamber is designed accordingly, preferably such that the removal and control opening, which may also be referred to as control openings, are not affected by the opening mechanism. In particular, they are not affected by openings in the sealing foil itself or by an opening mechanism of the apparatus which produces such openings. This may be achieved for example by removing a sealing foil entirely from the control openings before the medicament is taken out, or by making an opening in a sealing foil so big that its effect on the control openings is negligible.

In one embodiment of the magazine, a medicament is emptied into a preliminary chamber, the preliminary chamber having a corresponding control and removal opening which is connected to a vacuum flow for removing the medicament. For this purpose, a medicament may be sealed in its own medicament chamber with a sealing foil which is preferably opening by an opening means that may be installed in the chamber itself. In this embodiment this fill opening is arranged substantially on the same side as the control openings. The preliminary chamber may be an integral part of the medicament chamber or the medicament magazine, or it may be an integral part formed on an air channel. The advantage of the first variant is that a new unused chamber is available each time medicament is taken.

In a preferred embodiment of the inhaler, two medicament chambers are joined together through a common mouthpiece. In this way, the number of single doses of medicament can be doubled. For this, the individual medicament chambers of the two magazines are preferably arranged offset from one another. However, it is also possible, when removing the medicament, to open one chamber of each magazine and take one medicament from each. This is particularly advantageous if two medicaments have to be taken which cannot be stored together, or if every second time a double quantity of a medicament or medicament mixture has to be taken.

For producing a medicament magazine and optionally also certain parts of a device, pharmaceutically permitted materials are preferably used. The films used may be multi-layer films, for example, which are suitable as films for peeling or piercing or for scraping off. Multi-layer films usually have a layer of PE, PP or PVC and an aluminium layer. Depending on the particular requirement, a film is made more stable or tear-resistant, and this is pref done by incorporating a PET layer. In preferred material combinations, an outer layer of a film comprises the same material as an injected-moulded magazine, for example. In this way it is possible to seal or weld the different elements of a medicament magazine with the same materials. It is also possible to use sealing lacquer, e.g. heat-sealing lacquer. As a result, there are more possible material combinations for the individual elements. A sealing lacquer is applied, for example, to a film and/or to a magazine that is to be closed off. It is also possible for a foil to have a layer of sealing lacquer directly. The strength of the seal is preferably also optimally tailored to the use, so that, for example, a peelable film adheres directly but removably to an elements which is to be sealed.

The compounds specified below may be used in the apparatus according to the invention on their own or in combination. In the compounds specified below, W is a pharmacologically active substance and (for example) is selected from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the apparatus accin. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinoline-2-one 4-hydroxy-7-[2-{[2-{[3-(2-phenylethoxy)propyl] sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino] ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-on 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1,1dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol

[3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide 4-(2-{6-[4-(3-cyclopentanesulphonyl-phenyl)-butoxy]-hexylamino}-1-hydroxy-ethyl)-2-hydroxymethyl-phenol N-adamantan-2-yl-2-(3-{2-[2-hydroxy-2-(4-hydroxy-3-hydroxymethyl-phenye-ethylamino]-propyl}-phenyl)-acetamide, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

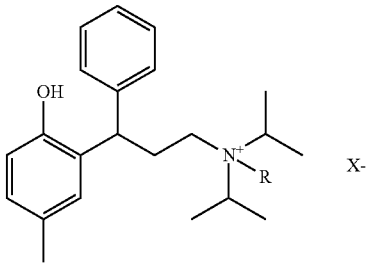

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-ene

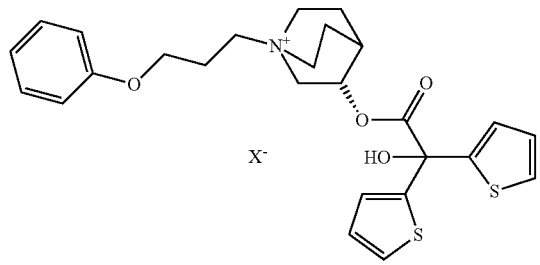

AC-1-ene wherein X⁻ may have the above-mentioned meanings. Other preferred anticholinergics are selected from the salts of formula AC-2

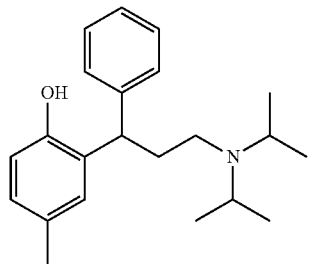

AC-2 wherein R denotes either methyl or ethyl and wherein X⁻ may have the above-mentioned meanings. In an alternative embodiment the compound of formula AC-2 may also be present in the form of the free base AC-2-base.

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;

cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3S-yl)6,9-difluoro-11-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tetramethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325, 366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the PDE4 inhibitors are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methyl ethyl)phenyl)propyl)thio)methyl)cyclopropane acetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention these acid addition salts are preferably selected from among the hydrochloride, hydrobromide, hydroiodide, hydrosulphate, hydrophosphate, ydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]amino}-7-cyclopropylmethoxy-quinazoline 4-[(3-chloro-4-fluorophenyl)amino]-6-{[4-(N,N-diethylamino)-1-oxo-2-buten-1-yl]-amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6,7-bis-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yl-oxy}-7-methoxy-quinazoline 4-[(3-chloro-4-fluoro-phenyl)amino]-6-{1-[(methoxymethyl)carbonyl]-piperidin-4-yl-oxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethansulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetinden, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

In addition, inhalable macromolecules may be used as disclosed in EP 1 003 478.

In addition, the compound may from the group of the derivatives of ergot alkaloids, triptanes, CGRP-inhibitors, phosphodiesterase-V inhibitors, optionally in the form of the racemates, enantiomers or diastereomers thereof, optionally in the form of the pharmacologically acceptable acid addition salts, solvates and/or hydrates thereof. Examples of ergot alkaloid derivatives are: dihydroergotamine, ergotamine.

Examples of substances suitable for inhalation include medicaments, medicament formulations and mixtures containing the above-mentioned active substances, and the salts and esters thereof and combinations of these active substances, salts and esters.

The invention is hereinafter described in more detail by means of examples. In the drawings:

BRIEF DESCRIPTION THE DRAWINGS

Figure 6:
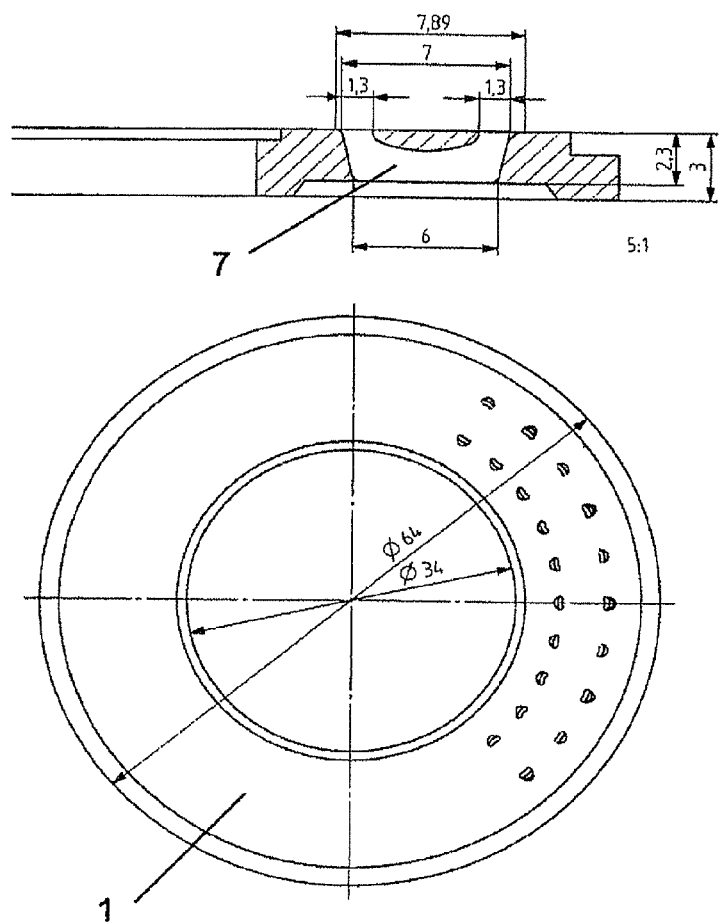
Figure 7:
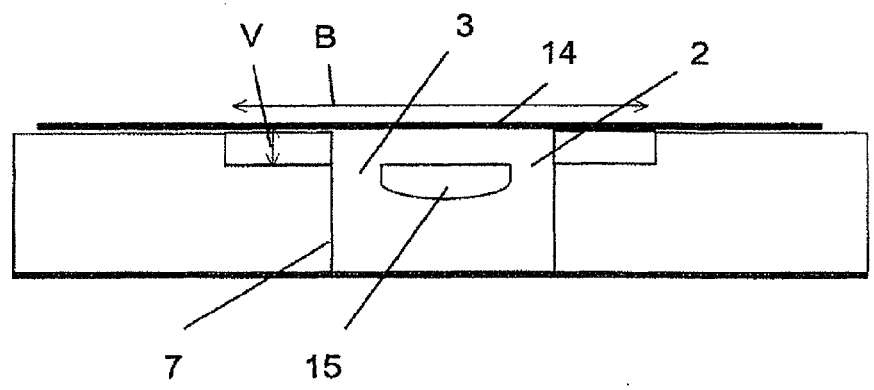
Figure 8:
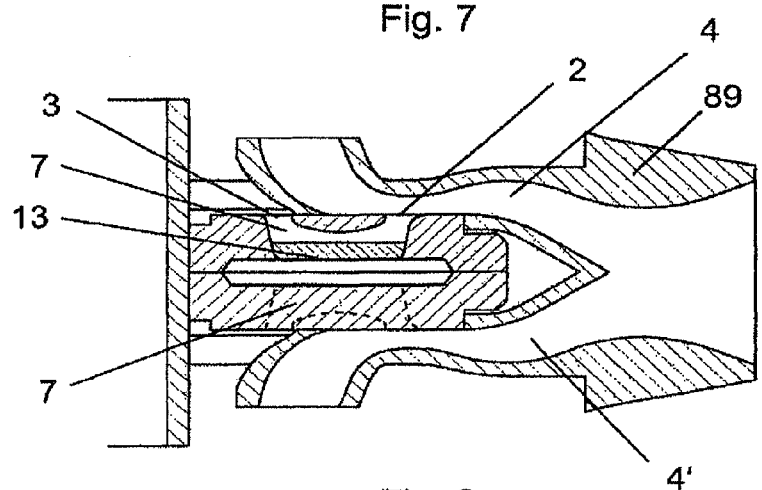
Figure 9:
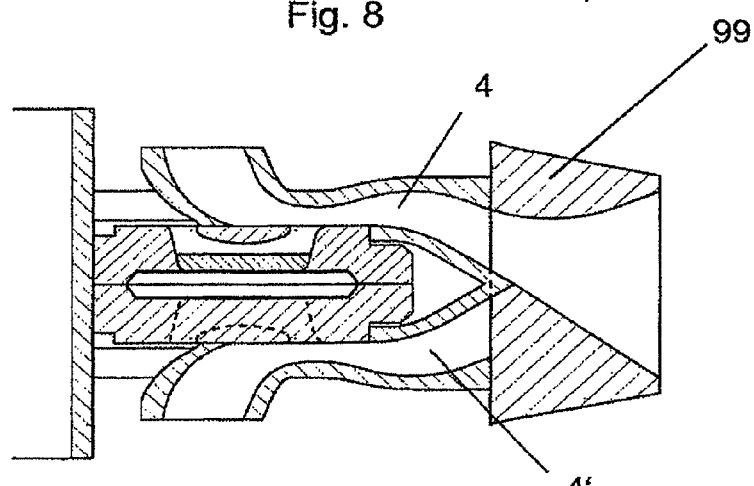
Figure 10:
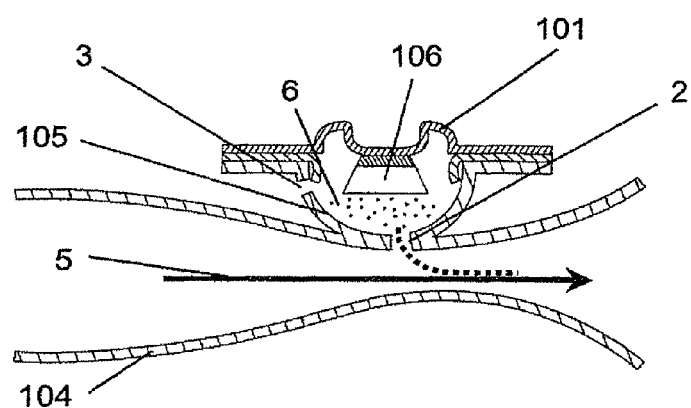
Figure 11:
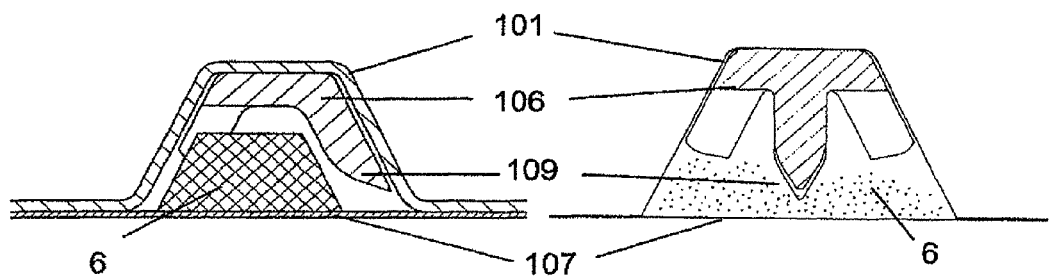

FIG. 6 shows a scale representation of the medicament magazine according to FIG. 3-5, FIG. 7 shows a medicament chamber for different opening mechanisms, FIG. 8 shows a double annular magazine with a combined air channel, FIG. 9 shows a double annular magazine with separate air channels, FIG. 10 shows a blister with internal structure and preliminary chamber as a medicament magazine, FIG. 11 shows two embodiments of a blister with internal structure.

DETAILED DESCRIPTION OF THE INVENTION

Figure 1:
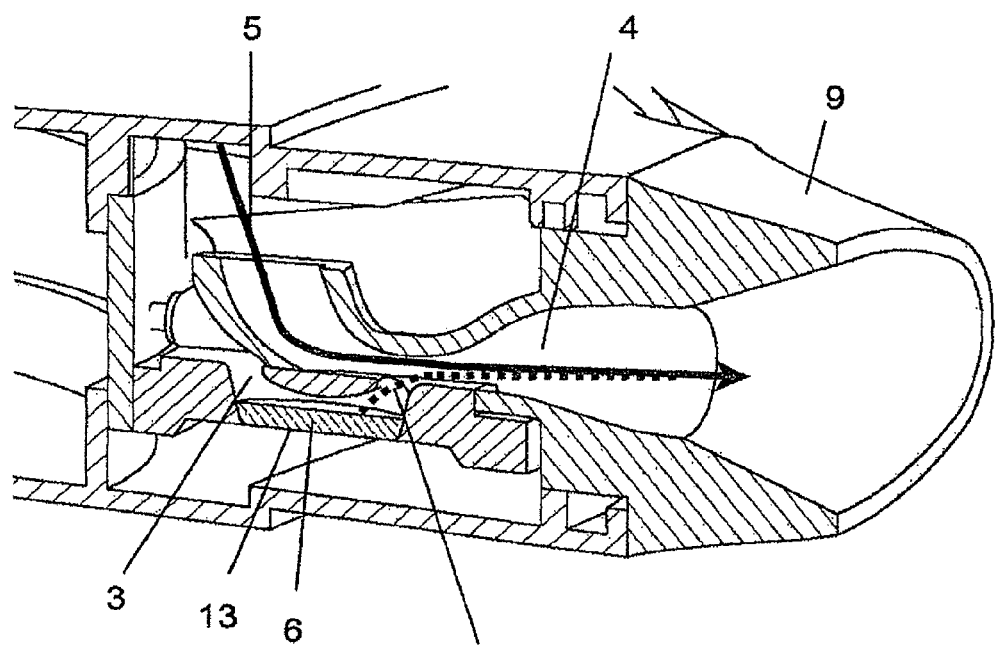
FIG. 1 shows a detail of a powder inhaler with the removal principle.
Figure 2:
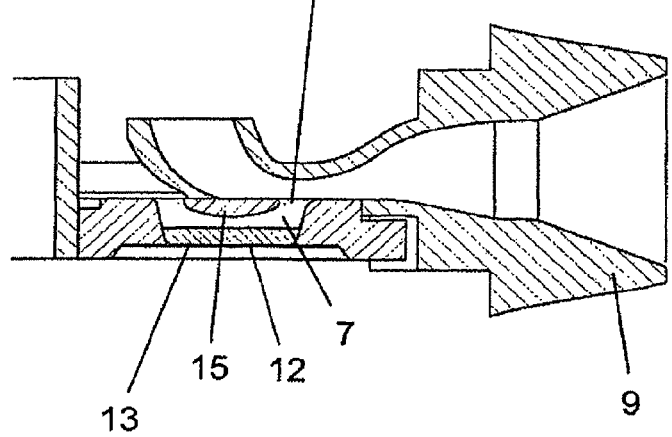
FIG. 2 shows the removal principle, in simplified view.
Figure 3:
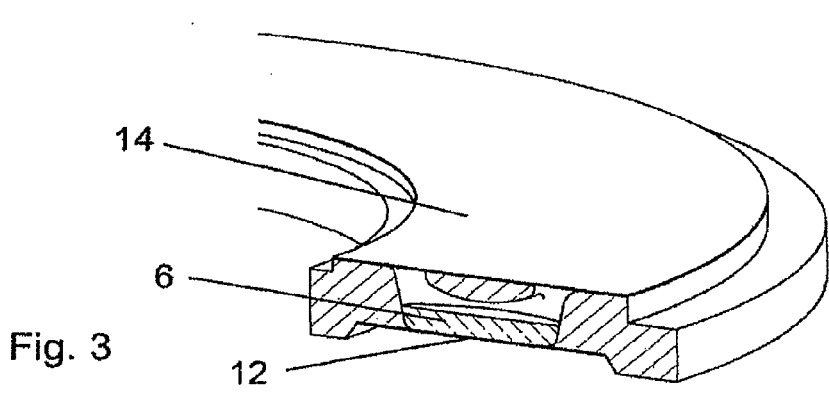
FIG. 3 shows a medicament magazine as an annular disc.
Figure 4:
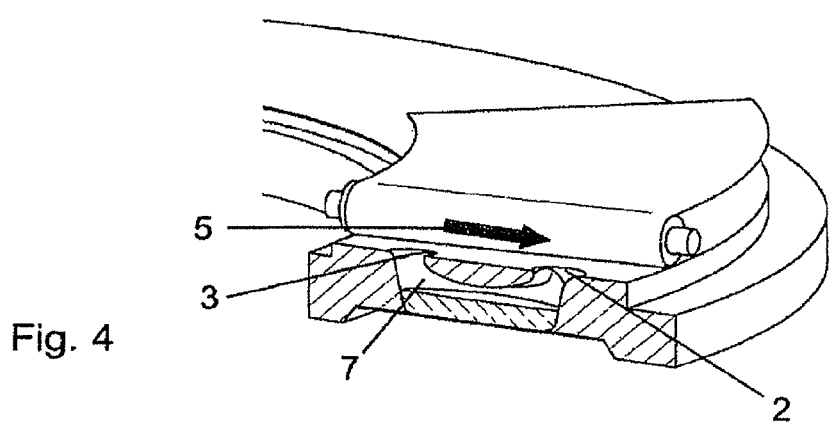
FIG. 4 shows the medicament magazine with the medicament chamber open.
Figure 5:
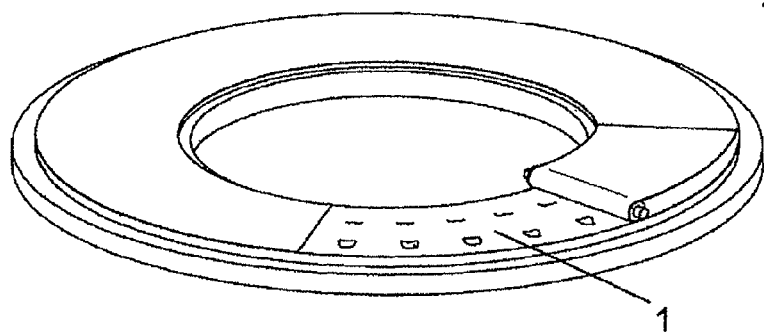
FIG. 5 shows the entire medicament magazine.

FIG. 1 and FIG. 2 show the removal principle for a powder 6 containing a medicament and contained in a medicament chamber, such as may be used in a powder inhaler. The medicament chamber is in the form of a cavity 7 in a plastics part preferably produced by injection moulding or thermoforming. The medicament chamber has, on an upper side, a removal opening 2 which is connected directly to an air channel 4. The air channel is constructed as a Venturi tube. When the inhaler is used, sucking on a mouthpiece 9 produces a drive current 5 in the air channel and a vacuum current in the region of the constriction of the air channel (Venturi effect). The powder in the cavity is sucked out into the air channel 4 through the removal opening and together with the drive current 5 is carried towards the mouthpiece and the person using the inhaler. As a result of the Venturi effect the maximum pressure difference and the maximum velocity in the air current are found at the removal opening. This guarantees efficient detachment of a medicament from its support (dispersion of the powder). The medicament chamber also has on its upper side, the same side as the removal opening, a control opening 3 through which air flows into and through the cavity and forms an emptying current. Some of this emptying current flows away over the powder 6 and can produce an additional Venturi effect with a turbulence element 15 located in the cavity between the turbulence element and the powder or the base of the cavity. The turbulence element may also have structures, e.g. projections pointing into the medicament chamber, which intensify the turbulence of the air and powder.

Every one of these measures and effects increases the formation of turbulence in the cavity and hence the dispersion. Any clumps in the powder can also be broken up in this way. The shape of the removal opening and the combining of the vacuum and emptying currents also influence the dispersion of the powder.

The medicament chamber comprises a fill opening 13 on the bottom, opposite the top. The fill opening 13 extends substantially over the entire lower surface of the cavity and is closed off with a sealing film 12 once the powder has been placed in the cavity.

With this removal concept the removal of the medicament can be adapted very sensitively and in versatile manner to all kinds of medicaments, dosages and user requirements. This can be done by varying and adapting the emptying flow, which is affected by several parameters: the diameter of the air channel above the removal opening, the dimensions of the removal opening, the configuration of the cavity, and the dimensions of the control opening. The special configuration of the medicament magazine also allows easy adaptation to different amounts, compositions or consistencies of medicaments, e.g. by enlarging the cavity and/or changing the opening diameter. The separate fill opening also allows this to be made as large as possible, so that a powder can be poured in very quickly and without having to be tailored to a special (small) fill opening. Also, because of the direct connection of a removal opening to the air channel and the vacuum flow prevailing therein, no powder is lost along lengthy passages or ducts.

If required, the air channel 4 has additional sidestream or bypass openings which terminate in the air channel and are arranged offset downstream of a removal opening, towards the mouthpiece 9. This reduces the suction force needed or creates crosscurrents in the air channel to assist with the dispersion of a powder contained therein.

FIG. 5 shows a multi-dose medicament magazine constructed as an annular magazine 1, of the kind that may be used in a disc-type inhaler, for example. In the annular magazine 1 the upper sealing film has been removed from five medicament chambers. The plan view shows one removal and one control opening for each medicament chamber. An annular magazine of this kind may be made in one piece by injection moulding, for example. The upper sealing film is applied first. After filling, the cavity is closed off by means of the lower sealing film. Examples of preferred injection-moulding materials are PE, PP and PVC.

FIGS. 3 and 4 each show a diagonal view of a medicament chamber, shown cut away. FIG. 3 shows a filled medicament chamber in which there is powder 6 in the cavity 7. The removal and control openings are covered by the upper sealing film 14 and are closed off thereby in airtight and watertight manner. The lower fill opening, one of which is preferably provided for each cavity, is closed off by a lower sealing film 12. FIG. 4 shows the same diagonal view of a medicament chamber after use. The upper sealing film 14 has been removed. The air flow 5 over the removal opening is guided through a constriction in the channel (cf. FIGS. 1 and 2), thereby producing a vacuum above this opening. The dimensions of the removal and control opening are preferably such that the cavity is emptied as continuously as possible.

FIG. 6 shows a cross-section through a cavity, and a plan view of an annular magazine, drawn to scale, such as might be produced for a powder volume of about 10 mm$^3$ and 30 cavities, i.e. single doses, in an annular magazine.

The quantity of fill volume of a single dose may be varied relatively easily by changing the depth and/or length of the cavity. As only the removal opening can be connected to a vacuum flow, the control opening can be arranged virtually anywhere in the magazine. It must not be adjacent to the removal opening on the same side of the annular magazine but it could, for example, be arranged on an inner diameter of the magazine.

FIG. 7 diagrammatically shows a section through the structure of a medicament chamber, as it might be designed in order to be opened by different opening mechanisms, such as peeling, scraping off or piercing, without affecting the control openings, i.e. the control and removal opening. FIG. 7 shows a cavity 7 with the removal and control opening 2, 3 spaced apart from each other. The openings are set into a recess. The height V and width B of the recess can be adapted to the particular opening mechanism. If the openings are exposed by peeling off a sealing film applied earlier, the height V of the recess is preferably zero and the width B (or area) of the recess corresponds to the width of the chamber. In known piercing processes, a sealing film would be pierced and the size and shape of a removal opening and a control opening would be determined by the piercing tools. These are generally inexact and a throttled flow would not be defined and in particular would not be reproducible. In order to be able to use piercing as the opening mechanism and thereby make use of the precisely defined openings that can be made when the product is manufactured by the injection moulding technique, the recess depth V>0 and the width B is chosen to be greater than the chamber width. As a result, piercing takes place independently of the actual removal and control opening. The piercing tool is selected such that the foil is pierced over one or more areas which are greater than the area of the removal and control opening, such that any influence of the pierced opening(s) is negligibly small in relation to the control openings.

FIGS. 8 and 9 each show a section through a double medicament magazine, e.g. an annular magazine. The magazine substantially corresponds to two annular magazines according to FIG. 3 which are arranged with their reverse sides, i.e. the sides containing the fill openings 13, touching in mirror image and are attached to one another or only pressed together. The two parts of the magazine are pushed together such that the individual medicament chambers 7 are not precisely opposite one another (the offset chamber is shown by dotted lines). In this way, a multi-dose inhaler of for example 30 doses can be converted into a preferred 60-dose inhaler. In FIG. 8 two air channels 4, 4', which belong to an upper and lower part of the magazine, open into the same mouthpiece 89. The mouthpiece and air channels are made in one piece. Because of the offset arrangement of the medicament chambers 7 (shown by dotted lines in FIG. 7) powder can only be taken from one chamber, even when the chambers are open. The air channel 4' which is not in use can be used for an additional air supply (bypass). However, it is also possible to arrange the chambers so that they are not offset from one another, so that two different medicaments, for example, can be taken from two chambers. FIG. 9 shows a mouthpiece 99 which subdivides the two air channels 4,4' so that no air can pass through a non-selected channel into the mouthpiece 99. The mouthpiece may be rotated for example from an upper part to a lower part of the magazine.

FIG. 10 shows another embodiment of the invention by reference to a medicament magazine which is constructed as a foil blister with an internal structure 101. This internal structure 106 has opening means, for example, in the form of piercing points or cutting edges by means of which a sealing foil that closes off a medicament chamber is opened by pressing the internal structure outwards. The internal structure is preferably also constructed so that it gives a degree of stability to the medicament chamber. In this way, a powder contained therein is protected from mechanical influences from the outside or, in particular, when the chamber is opened. This is important for powdered medicament carriers for inhalers, as the inhaling or dosing of a compacted powder is no longer possible, or is no longer possible in a defined manner.

The foil blister 101 has, in the region of the actual medicament chamber, a preliminary chamber 105. The preliminary chamber 105 has a removal opening 2 and a control opening 3. The delivery of the powder 6 from the blister is preferably effected as follows: the contents of the blister are emptied or introduced into the preliminary chamber 105 with the aid of the internal structure, preferably directly during the action of loading an inhaler. The preliminary chamber has a removal opening 2 which may be in the form of a through-bore and is connected to a Venturi suction tube 104. As a result of the Venturi effect, the maximum pressure difference is present at the through-bore, enabling the powder to be drawn out of the preliminary chamber 105 in metered amounts. At this point the air current 5 reaches its maximum speed, thus allowing efficient detachment (dispersion) of an active substance from the carrier.

Preferably a blister with an integrated preliminary chamber is produced, such that a medicament magazine with a fill opening, removal opening and control opening in turn forms a unit, while the openings are matched to one another, depending on the application. One advantage of this variant is that a fresh preliminary chamber is provided for each inhalation. Another variant in which a fresh suction tube or part of a suction tube is available for each removal is when the blister is formed with an integrated preliminary chamber and suction tube. Any medicament residues on the walls of the suction tube, which in particular occur directly in the region of the removal opening would thus not affect subsequent removals. In another variant the preliminary chamber is in turn an integral part of the suction tube, but is independent of the foil blister and the actual medicament chamber.

To illustrate blisters with an internal structure 101 FIG. 11 shows two examples on a larger scale. The Figure shows one medicament chamber in the filled, unused state in each case. Powder 6 is at least partly enclosed by the internal structure 3 and protected from external mechanical effects, but particularly from being compressed as the internal structure is pressed out of the medicament chamber. The internal structures have piercing points or cutting edges 109 with which a sealing foil 107 is pierced or cut open and torn or cut away as the chambers are opened.

The internal structure may be connected to the blister, e.g. sealed on its reverse side with a film so as not to fall into the preliminary chamber depending on the position of the blister. However, if the preliminary chamber is an integral part of the blister or each individual medicament chamber located therein, this measure may not be necessary. An internal structure of this kind may also serve as a turbulence element as well or in particular if it is freely positioned in the preliminary chamber. The internal structure may also provide additional turbulence by means of an emptying current passing through the preliminary chamber and thus additionally contribute to the disaggregation and dispersion of the powder. The internal structure is preferably very open in design, so that an air current can penetrate into and through the internal structure is possible from many sides. This contributes to emptying a medicament chamber as completely as possible and additional air turbulence.

The internal structure, preliminary chamber and suction tube are preferably formed by injection moulding a plastic. However, it is also possible to produce individual parts thereof by a thermoforming process or, in the case of internal structures, to stamp and form them from a foil, e.g. a metal foil.

What is claimed is:

1. Medicament dispensing device comprising a mouthpiece (9) and Venturi tube air channel (4) connected therewith, as well as a medicament magazine with a plurality of medicament chambers containing a medicament, each of the chambers having at least one removal opening for removal of the medicament and a fill opening, wherein a drive current comprising a vacuum flow can be generated in the Venturi tube air channel, characterised in that a most narrow region of the air channel produces the vacuum flow, is connected to the at least one removal opening (2) provided by the medicament magazine, this removal opening being connected to a control opening (3), to form an emptying current through the control opening via the removal opening, wherein the removal opening is connected to the control opening via the medicament chamber, wherein the removal opening is attachable to the vacuum flow to form an emptying current through the control opening to the removal opening, and wherein the removal opening, the control opening and the fill opening are spaced from one another.

2. Medicament dispensing device according to claim 1, wherein the control and removal openings (3, 2) are provided in the medicament magazine.

3. Medicament dispensing device according to claim 1, wherein a bypass opening (8) is provided in the air channel (4) for forming a bypass flow, the bypass opening being arranged downstream of the removal opening (2) in the direction of the mouthpiece (9).

4. Medicament dispensing device according to claim 1, having a throttle arrangement for varying the amount of medicament removed per unit of time.

5. Medicament dispensing device according to claim 4, wherein the throttle arrangement comprises the control opening (3), the removal opening (2), the inner configuration of the medicament chamber and the configuration of the air channel connected to the removal opening.

6. Medicament dispensing device according to claim 1, for administering a medicament that contains an active substance or a combination of active substances selected from among the group of betamimetics, anticholinergics, steroids, antiallergics, ergot alkaloid derivatives, triptanes, CGRP antagonists, the phosphodiesterase-V inhibitors, phosphodiesterase-IV inhibitors, LTD4-antagonists, EGFR-kinase inhibitors.

7. Medicament magazine (1) comprising a plurality of medicament chambers having at least one opening for the removal (2) of a medicament, characterised in that each medicament chamber has a fill opening (13) and the removal opening (2), the removal opening (2) being connectable to a vacuum flow in a Venturi tube to produce an emptying current through the control opening (3) across the medicament chamber to the removal opening (2) by a drive current which bypasses the medicament chamber and delivers the medicament, wherein the removal opening (2) and control opening (3) are integrated and predefined in the medicament magazine, and wherein the removal opening, the control opening and the fill opening are spaced from one another.

8. Medicament magazine according to claim 7, wherein the magazine is annular and a plurality of medicament chambers are arranged in a ring in the magazine.

9. Medicament magazine according to claim 7, wherein the fill opening (13) is arranged in a side of the magazine opposite the removal and control opening (2, 3).

10. Medicament magazine according to claim 7, wherein the fill opening (13) is arranged on the same side of the magazine as the removal and control opening (2, 3).

11. Medicament magazine according to claim 7, wherein a turbulence element (7) is arranged in the medicament chamber.

12. Medicament magazine according to claim 11, wherein the turbulence element (7) is formed by at least a part of the wall of the medicament chamber.

13. Medicament magazine according to claim 7, is a one piece injection molded part.

14. Multi-dose powder inhaler comprising a medicament magazine according to claim 7.

15. Multi-dose powder inhaler according to claim 14, comprising 60 medicament chambers with single doses of medicament.

16. Method of removing a medicament from a medicament chamber, wherein a medicament is removed from the medicament chamber by the formation of a vacuum flow via a Venturi tube air channel, and wherein a drive current is produced in the Venturi tube air channel by a user sucking on a mouthpiece so that the vacuum flow produces an emptying current through the medicament chamber via a control opening through which air flows into and through the medicament chamber to a removal opening, characterised in that the vacuum flow is connected to the removal opening (2), defined by the medicament magazine, which removal opening is connected to the medicament chamber and is spaced from the control opening and a fill opening, wherein the emptying current is not connected with the drive current until it exits the medicament chamber.

17. Method according to claim 16, wherein the quantity of medicament to be removed per unit of time is determined by the strength of the emptying current, while the latter can be varied by means of a throttle arrangement.

18. Method according to claim 16, wherein at least some of the emptying current flows away over the medicament contained in the medicament chamber.

19. Method according to claim 16, wherein an additional vacuum flow in the medicament chamber is produced by means of an inner configuration of the medicament chamber.

20. Method according to claim 16, wherein a medicament is emptied into a preliminary chamber (105) which is attached to a vacuum flow via a removal opening (2) for the removal of the medicament.

21. Method according to claim 16, wherein a medicament chamber is opened before the removal of medicament, by piercing, scraping off or peeling a sealing foil (14) that closes off the medicament chamber.

* * * * *